(12) United States Patent
Hillukka

(10) Patent No.: US 10,182,911 B2
(45) Date of Patent: Jan. 22, 2019

(54) DEVICES AND METHODS FOR TRANSCATHETER HEART VALVE DELIVERY

(71) Applicant: St. Jude Medical, Cardiology Division, Inc., St. Paul, MN (US)

(72) Inventor: Brett Allen Hillukka, Hanover, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 775 days.

(21) Appl. No.: 14/295,576

(22) Filed: Jun. 4, 2014

(65) Prior Publication Data

US 2014/0364940 A1 Dec. 11, 2014

Related U.S. Application Data

(60) Provisional application No. 61/831,293, filed on Jun. 5, 2013.

(51) Int. Cl.
*A61F 2/24* (2006.01)
*A61B 1/00* (2006.01)
*A61F 2/95* (2013.01)

(52) U.S. Cl.
CPC .......... *A61F 2/2436* (2013.01); *A61B 1/0014* (2013.01); *A61B 1/00128* (2013.01); *A61F 2002/9517* (2013.01); *Y10T 29/49947* (2015.01)

(58) Field of Classification Search
CPC ... A61B 1/00128; A61B 1/0014; A61B 90/57; A61F 2/95; A61F 2/2427; A61F 2/2436; A61F 2002/9517; A61M 25/02; A61M 2025/024; A61M 2025/028

See application file for complete search history.

(56) References Cited

U.S. PATENT DOCUMENTS

| | | | |
|---|---|---|---|
| 4,423,730 A | 1/1984 | Gabbay | |
| 5,924,424 A | 7/1999 | Stevens et al. | |
| 5,968,068 A | 10/1999 | Dehdashtian et al. | |
| 6,306,141 B1 | 10/2001 | Jervis | |
| 2006/0106415 A1 | 5/2006 | Gabbay | |
| 2006/0135947 A1* | 6/2006 | Soltesz | A61B 17/12104 604/516 |
| 2006/0142848 A1 | 6/2006 | Gabbay | |
| 2006/0167468 A1 | 7/2006 | Gabbay | |

(Continued)

FOREIGN PATENT DOCUMENTS

| | | |
|---|---|---|
| EP | 1129744 A1 | 9/2001 |
| EP | 1157673 A2 | 11/2001 |

(Continued)

*Primary Examiner* — Katherine Rodjom
(74) *Attorney, Agent, or Firm* — Lerner, David, Littenberg, Krumholz & Mentlik, LLP

(57) ABSTRACT

A clip for use during the loading of a prosthetic heart valve into a delivery device having an operating handle, a catheter assembly having a compartment for receiving the prosthetic heart valve, and an outer shaft joining the catheter assembly to the operating handle. The clip includes a first receiver coupleable to the operating handle of the delivery device and a second receiver coupleable to the outer shaft of the delivery device. The first and second receivers may be arranged orthogonally to one another so that in use the clip orients the catheter assembly substantially orthogonally to the operating handle.

9 Claims, 6 Drawing Sheets

(56) References Cited

U.S. PATENT DOCUMENTS

| | | |
|---|---|---|
| 2007/0073391 A1 | 3/2007 | Bourang et al. |
| 2007/0088431 A1 | 4/2007 | Bourang et al. |
| 2007/0112422 A1 | 5/2007 | Dehdashtian |
| 2007/0162100 A1 | 7/2007 | Gabbay |
| 2007/0168013 A1 | 7/2007 | Douglas |
| 2007/0203575 A1 | 8/2007 | Forster et al. |
| 2007/0239271 A1 | 10/2007 | Nguyen |
| 2008/0147182 A1 | 6/2008 | Righini et al. |
| 2009/0054975 A1 | 2/2009 | del Nido et al. |
| 2010/0198006 A1* | 8/2010 | Greenburg ......... A61B 1/00128 600/104 |
| 2011/0125133 A1* | 5/2011 | Aggerholm ....... A61M 25/0097 604/523 |
| 2011/0224678 A1 | 9/2011 | Gabbay |
| 2014/0155990 A1* | 6/2014 | Nyuli ................... A61F 2/2418 623/2.11 |

FOREIGN PATENT DOCUMENTS

| | | |
|---|---|---|
| WO | 2010051025 A1 | 5/2010 |
| WO | 2010087975 A1 | 8/2010 |

\* cited by examiner

DEVICES AND METHODS FOR TRANSCATHETER HEART VALVE DELIVERY

CROSS-REFERENCES TO RELATED APPLICATIONS

The present application claims the benefit of the filing date of U.S. Provisional Patent Application No. 61/831,293 filed Jun. 5, 2013, the disclosure of which is hereby incorporated herein by reference.

BACKGROUND OF THE INVENTION

The present invention is related to prosthetic heart valve replacement, and more particularly to devices, systems, and methods for transcatheter delivery of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

Despite the various improvements that have been made to the collapsible prosthetic heart valve delivery process, conventional delivery devices, systems, and methods suffer from some shortcomings. For example, in conventional delivery devices for self-expanding valves, it may be difficult to load a prosthetic heart valve into the current delivery device. Specifically, due to the length of the delivery system, it is common for two or more operators to load the prosthetic heart valve into the delivery device.

There therefore is a need for further improvements to the devices, systems, and methods for transcatheter delivery of collapsible prosthetic heart valves, and in particular, the loading of such prosthetic heart valves. Among other advantages, the present invention may address one or more of these needs.

BRIEF SUMMARY OF THE INVENTION

In another example, a method of loading a collapsible prosthetic heart includes providing a delivery device having a catheter assembly, an operating handle and an outer shaft extending therebetween, the catheter assembly including a compartment adapted to receive the prosthetic heart valve and being spaced from the operating handle by a length of the outer shaft. The outer shaft may be coupled to a clip so that the catheter assembly is at a fixed distance from the operating handle, the fixed distance being less than the length of the outer shaft. The prosthetic heart valve may be loaded into the compartment of the catheter assembly.

In another example, a loading clip for a delivery device having an operating handle and an outer shaft extending from an end of the operating handle includes a body having a first receiver and a second receiver, the first receiver being coupleable to a portion of the delivery device, and the second receiver being coupleable to a portion of the outer shaft of the delivery device.

In another example, a loading clip for a delivery device includes a body having a first receiver and a second receiver joined to the first receiver at a neck, the first receiver having a first receiving space configured to accept a first portion of an outer shaft of the delivery device and the second receiver having a second receiving space configured to accept a second portion of the outer shaft of the delivery device.

In one example, a delivery device for a collapsible prosthetic heart valve includes a catheter assembly having a compartment for receiving a medical device and an outer shaft having a first end coupled to the catheter assembly. The device further includes an operating handle including a deployment actuator coupled to a second end of the outer shaft, the operating handle having a clip for holding an intermediate portion of the outer shaft in fixed relationship to the operating handle.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

DETAILED DESCRIPTION

As used herein, the terms "proximal" and "distal" are to be taken as relative to a user using the disclosed delivery devices. "Proximal" is to be understood as relatively close to the user and "distal" is to be understood as relatively farther away from the user.

Figure 1A:
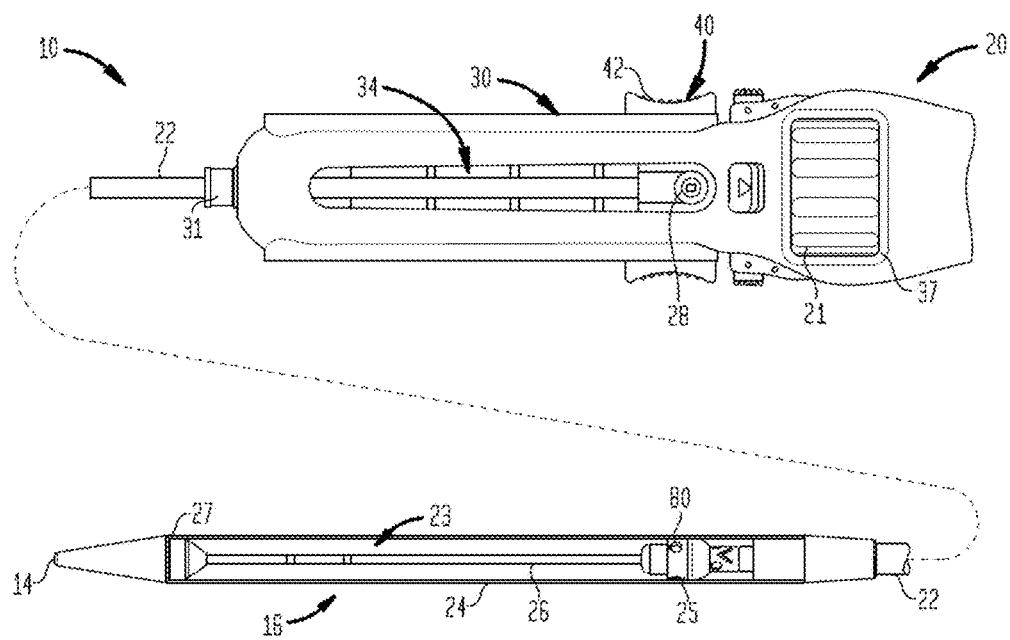
FIG. 1A is a top plan view of a portion of an operating handle of a transfemoral delivery device for a collapsible prosthetic heart valve, shown with a partial longitudinal cross-section of the distal portion of a transfemoral catheter assembly.
Figure 1B:
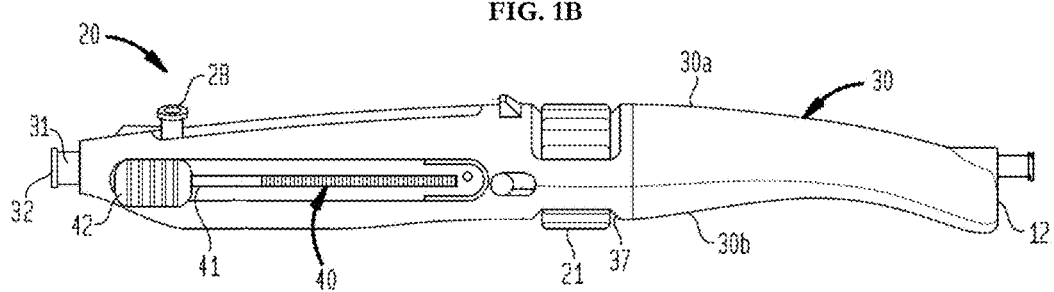
FIG. 1B is a side view of the handle of FIG. 1A.

Referring now to FIGS. 1A and 1B, the structure and function of a transfemoral delivery device will be described. It will be understood, however, that the devices and methods disclosed herein also may be used with a transapical or transseptal delivery device. An exemplary transfemoral delivery device 10 for a collapsible prosthetic heart valve (or other types of self-expanding collapsible stents) has a catheter assembly 16 for delivering the heart valve to and deploying the heart valve at a target location, and an operating handle 20 for controlling deployment of the valve from the catheter assembly. Delivery device 10 extends from a proximal end 12 to an atraumatic tip 14 at the distal end of catheter assembly 16. Catheter assembly 16 is adapted to receive a collapsible prosthetic heart valve (not shown) in a compartment 23 defined around an inner shaft 26 and covered by a distal sheath 24.

Inner shaft 26 may extend from operating handle 20 to atraumatic tip 14 of the delivery device, and may include a retainer 25 affixed thereto at a spaced distance from tip 14 and adapted to hold a collapsible prosthetic valve in compartment 23. Retainer 25 may have recesses 80 therein that are adapted to hold corresponding retention members of the valve. Inner shaft 26 may be made of a flexible material such as braided polyimide or polyetheretherketone (PEEK), for example. Using a material such as PEEK may improve the resistance of inner shaft 26 to kinking while catheter assembly 16 is tracking through the vasculature of a patient.

Distal sheath 24 surrounds inner shaft 26 and is slideable relative to the inner shaft such that it can selectively cover or uncover compartment 23. Distal sheath 24 is affixed at its proximal end to an outer shaft 22, the proximal end of which is connected to operating handle 20 in a manner to be described. Distal end 27 of distal sheath 24 abuts atraumatic tip 14 when the distal sheath is fully covering compartment 23, and is spaced apart from the atraumatic tip when compartment 23 is at least partially uncovered.

Operating handle 20 is adapted to control deployment of a prosthetic valve located in compartment 23 by permitting a user to selectively slide outer shaft 22 proximally or distally relative to inner shaft 26, thereby respectively uncovering or covering the compartment with distal sheath 24. Outer shaft 22 may be made of a flexible material such as nylon 11 or nylon 12, and it may have a round braid construction (i.e., round cross-section fibers braided together) or flat braid construction (i.e., rectangular cross-section fibers braided together), for example.

The proximal end of inner shaft 26 may be connected in a substantially fixed relationship to an outer housing 30 of operating handle 20, and the proximal end of the outer shaft 22 may be affixed to a carriage assembly 40 that is slideable along a longitudinal axis of the handle housing, such that a user can selectively slide the outer shaft relative to the inner shaft by sliding the carriage assembly relative to the housing. Operating handle 20 may further include a hemostasis valve 28 having an internal gasket adapted to create a seal between inner shaft 26 and the proximal end of outer shaft 22.

As shown, handle housing 30 includes a top portion 30a and a bottom portion 30b. Top and bottom portions 30a and 30b may be individual pieces joined to one another as shown in FIG. 1B. Collectively, top and bottom portions 30a and 30b define an elongated space 34 in housing 30 in which carriage assembly 40 may travel. Optionally, top and bottom portions 30a and 30b may further form a substantially cylindrical boss 31 for accepting a clip, as will be described below. Elongated space 34 preferably permits carriage assembly 40 to travel a distance that is at least as long as the anticipated length of the prosthetic valve to be delivered (e.g., at least about 50 mm), such that distal sheath 24 can be fully retracted from around the prosthetic valve. Carriage assembly 40 includes a pair of carriage grips 42, each attached to a body portion 41. Although the carriage assembly 40 is shown in FIGS. 1A and 1B as having two carriage grips 42, that need not be the case.

Handle housing 30 further defines a pocket 37 that extends through top portion 30a and bottom portion 30b for receiving a deployment actuator 21. Pocket 37 is sized and shaped to receive deployment actuator 21 with minimal clearance, such that the location of deployment actuator remains substantially fixed relative to housing 30 as it is rotated. Deployment actuator 21 may be internally coupled to body portion 41 via a threaded shaft or other suitable connection such that rotation of the deployment actuator in one direction (either clockwise or counterclockwise) pulls the body portion 41 of carriage assembly 40 proximally through elongated space 34.

To use operating handle 20 to deploy a prosthetic valve that has been loaded into compartment 23 and covered by distal sheath 24, the user may rotate deployment actuator 21, causing carriage assembly 40 to slide proximally within elongated space 34 in housing 30. Because distal sheath 24 is affixed to outer shaft 22, which in turn is affixed to carriage assembly 40, and because inner shaft 26 is fixed to housing 30, sliding the carriage assembly proximally relative to the housing will retract the distal sheath proximally from compartment 23, thereby exposing and initiating deployment of the valve located therein.

As seen in FIG. 1A, outer shaft 22 may be formed of a long and flexible tube and extend between operating handle 20 and catheter assembly 16. Outer shaft 22 may be between about 1.5 meters and about 2.5 meters in length. Due to its length, two operators are typically needed to load a prosthetic heart valve into compartment 23. Specifically, one operator may grasp operating handle 20, while another grasps catheter assembly 16 to load the prosthetic heart valve therein. To aid in loading a prosthetic heart valve into a delivery device, one or more of the disclosed loading clips may be used.

Figure 2A:
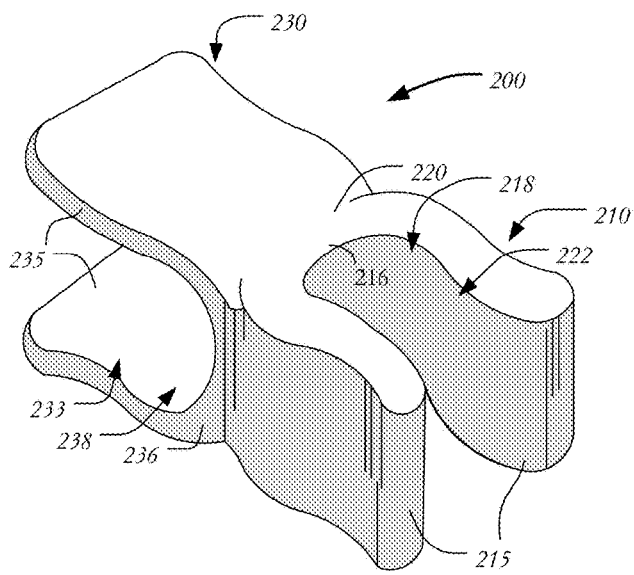
FIG. 2A is an isometric view of one embodiment of a clip.
Figure 2B:
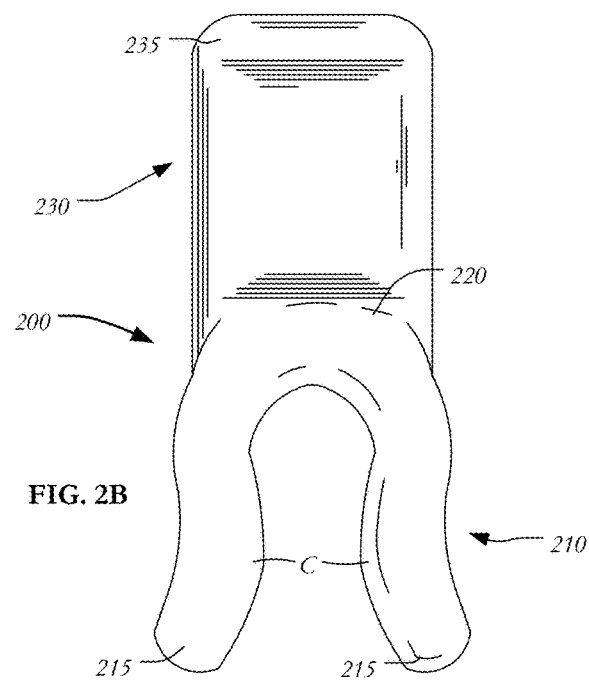
FIG. 2B is a top view of the clip of FIG. 2A.

FIGS. 2A and 2B illustrate one embodiment of a clip for use during the loading of a prosthetic heart valve into compartment 23 of catheter assembly 16. Clip 200 may be formed of any suitable polymeric material, such as, for example, acrylonitrile butadiene styrene (ABS) or other similar thermoplastic materials, a flexible metal or a suitable synthetic material. Clip 200 includes first receiver 210 connected via neck 220 to second receiver 230. First receiver 210 includes a pair of substantially tilde-shape fingers 215 connected to one another at a base 216 so as to define a receiving space 218 therebetween, providing receiver 210 with a generally horseshoe shape. Receiving space 218 is sized to accept an intermediate portion of outer shaft 22 of delivery device 10 therein (e.g., any portion of outer shaft 22 between operating handle 20 and catheter assembly 16). The inwardly curved portions of fingers 215 form a narrowed region 222 near the free ends of the finger so as to securely retain outer shape 22 in receiving space 218. Likewise, second receiver 230 includes a pair of substantially tilde-shaped fingers 235 connected to one another at a base 236 so as to define a receiving space 238 therebetween, providing receiver 230 with a generally horseshoe shape. Receiving space 238 is sized to accept another intermediate portion of outer shaft 22. The inwardly curved portions of fingers 235 form a narrowed region 233 near the free ends of the fingers so as to securely retain outer shaft 22 in receiving space 238. As seen in FIG. 2A, first receiver 210 and second receiver 230 are connected end-to-end at their respective bases 216, 236 one of the receivers being rotated approximately 90 degrees with respect to the other receiver such that fingers 215 are orthogonal to fingers 235.

Figure 2C:
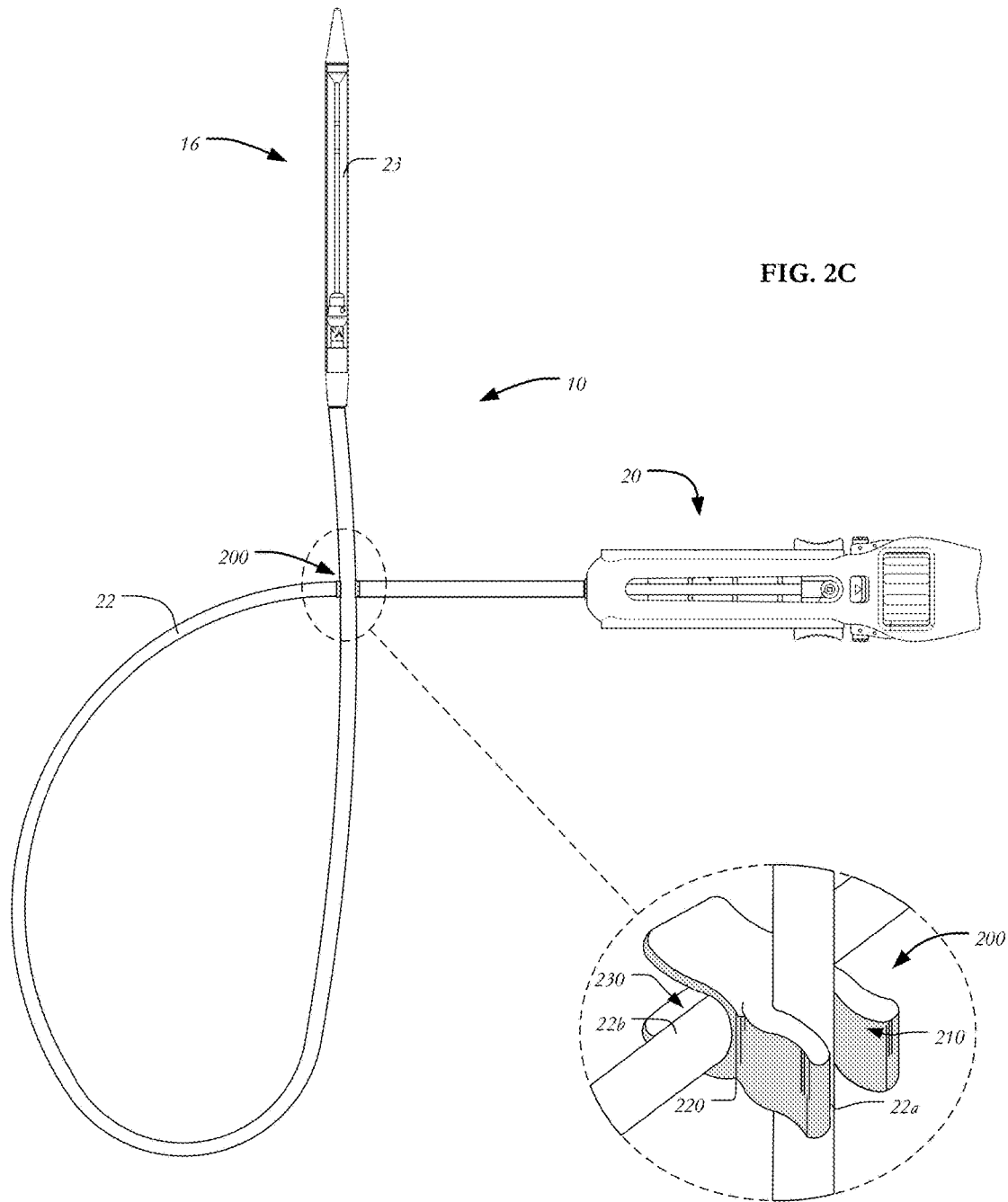
FIG. 2C illustrates the clip of FIGS. 2A and 2B being coupled to an outer shaft of the delivery device of FIGS. 1A and 1B.

FIG. 2C illustrates clip 200 coupled to outer shaft 22 of delivery device 10 at two different regions of the outer shaft. First receiver 210 accepts a first portion 22a of outer shaft 22 in receiving space 218, while second receiver 230 accepts a second portion 22b of outer shaft 22, remote from the first portion 22a, in receiving space 238. By holding these two remote portions of outer shaft 22 together, clip 200 shortens the overall length of delivery 10 making it easier to handle. Moreover, when first portion 22a of outer shaft 22 is near catheter assembly 16 and second portion 22b of outer shaft 22 is near operating handle 20, the connection of these portions to one another positions the operating handle near the catheter assembly, making it easier for a single operator to hold the operating handle while loading a prosthetic heart valve within compartment 23 of the catheter assembly. It will be understood that while outer shaft 22 is illustrated as forming a single loop between operating handle 20 and catheter assembly 16, multiple clips may be used and multiple loops may be formed. Additionally, clip 200 may be configured to have a receiver with a receiving space large enough to accept two or more portions of outer shaft 22. In such a case, a single clip may hold multiple loops of outer shaft 22.

Figure 3A:
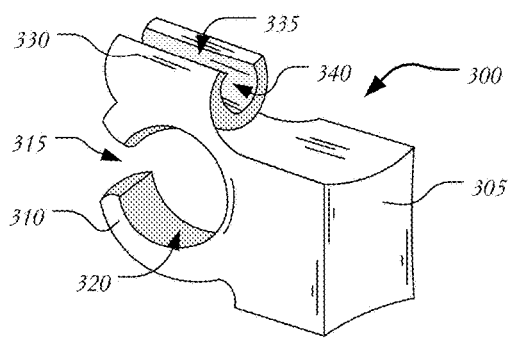
FIG. 3A is a perspective view of another embodiment of a clip.
Figure 3B:
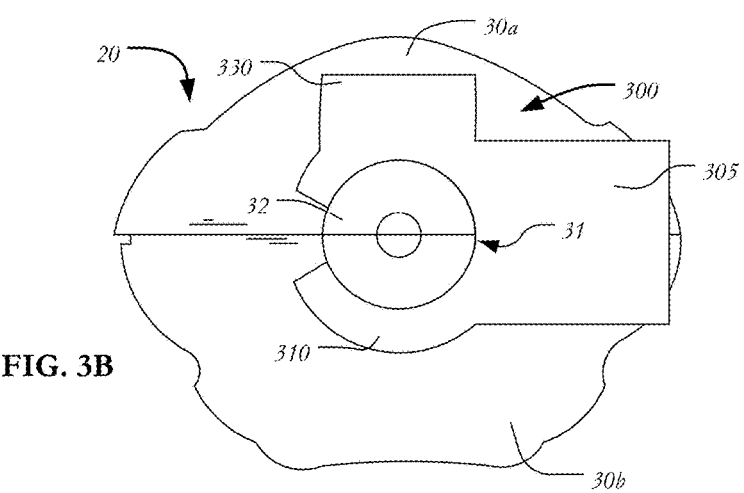
FIG. 3B is an end view showing the clip of FIG. 3A coupled to an operating handle of a delivery device.

FIGS. 3A and 3B illustrate another embodiment of a clip for use during the loading of a prosthetic heart valve into compartment 23 of catheter assembly 16. Clip 300 may be formed of any of the materials described above for forming clip 200 and may include body 305 having first receiver 310 and second receiver 330. First receiver 310 may be substantially ring-shaped with a round receiving space 320 sized and configured to accept a portion of housing 30 of delivery device 10. Specifically, first receiver 310 may have an opening to enable clip 300 to be coupled to and decoupled from boss 31 on outer housing 30.

Second receiver 330 may have a tube-like structure with an elongated receiving space 340 sized and configured to accept a portion of outer shaft 22. A longitudinal opening 335 in second receiver 330 enables clip 300 to be coupled to and decoupled from outer shaft 22. Second receiver 330 may be oriented relative to first receiver 310 such that the longitudinal axis of second receiver 330 is perpendicular to the longitudinal axis of first receiver 310. FIG. 3B is an end view showing clip 300 coupled to operating handle 20. Specifically, first receiver 310 is friction fit onto boss 31 with second receiver 330 extending upward, away from the bottom portion 30b of housing 30, for accepting a portion of outer shaft 22 (not shown in this figure). A raised annular lip 32 on the free end of boss 31 prevents clip 300 from sliding longitudinally off of the boss.

Figure 3C:
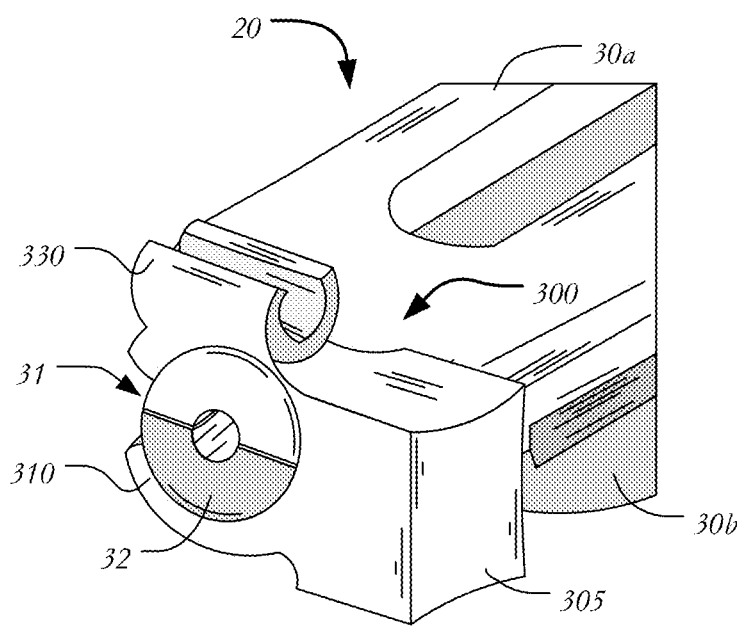
FIG. 3C is a perspective view of the clip of FIGS. 3A and 3B coupled to an operating handle of a delivery device.

FIG. 3C further illustrates clip 300 coupled to operating handle 20. When clip 300 is coupled to operating handle 20, second receiver 330 extends perpendicular to the longitudinal axis of operating handle 20. Therefore, when the intermediate portion of outer shaft 22 (not shown in this figure), which extends between the boss 31 on operating handle 20 and catheter assembly 16, is formed into a loop and accepted within second receiver 330, the catheter assembly will be oriented perpendicularly to the longitudinal axis of operating handle 20. Because first receiver 310 is oriented perpendicularly to second receiver 330, catheter assembly 16 and operating handle 20 form an L-shaped configuration when clip 300 is attached to outer shaft 22 and boss 31.

Figure 4A:
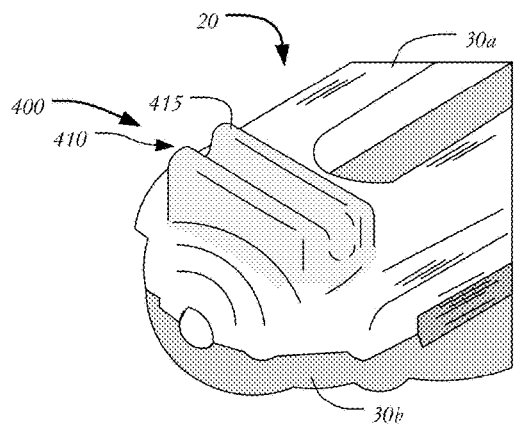
FIG. 4A is a partial perspective view showing an operating handle incorporating an integrally molded clip.
Figure 4B:
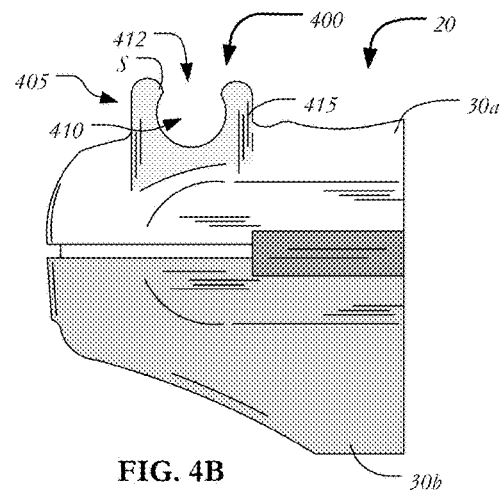
FIG. 4B is a partial side view of the operating handle incorporating the molded clip of FIG. 4A.
Figure 4C:
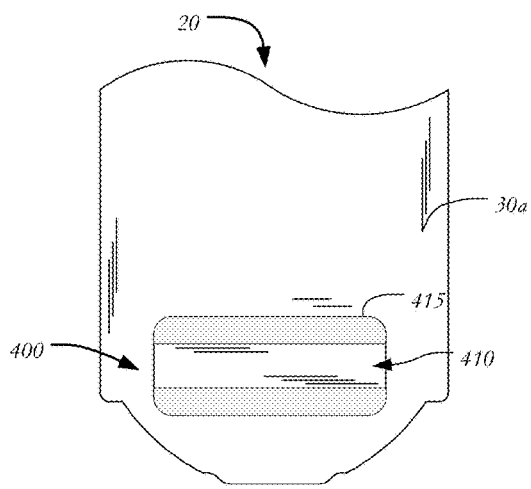
FIG. 4C is a partial top view of the operating handle incorporating the molded clip of FIG. 4A.

Though the clips have been illustrated herein as individual, discrete devices for removably coupling to an operating handle, FIGS. 4A-C illustrate another embodiment in which a clip is molded into and formed integrally with an operating handle. A molded clip eliminates the need for coupling the clip to and decoupling the clip from two components. Moreover, an integrally molded clip avoids the need to handle the clip and may reduce the risk of losing the clip during the valve loading procedure.

Clip 400 may include a single receiver 405 molded integrally with top portion 30a of handle housing 30. Receiver 405 may include a pair of parallel ridges 415 defining a trough-shaped receiving space 410 therebetween. Receiving space 410 may be sized and configured to accept outer shaft 22 (not shown) of delivery device 10. As best seen in FIG. 4B, ridges 415 define a generally cylindrical receiving space 410 of greater than 180°, thereby forming a narrowed opening 412 with shoulders S that secure outer shaft 22 in the receiving space. When outer shaft 22 is coupled within receiver 405, the outer shaft 22 is interference fit and remains coupled until the operator pulls it out of the receiver. As shown, ridges 415 may be disposed perpendicularly to the longitudinal axis of operating handle 20. Thus, receiver 405 is configured to accept outer shaft 22 such that the catheter assembly (not shown) is oriented orthogonally to operating handle 20. It will be understood, however, that ridges 415 may be oriented such that catheter assembly 16 forms a 25, 30, 40, 45 or 60 degree angle, or any other angle, with operating handle 20 when outer shaft 22 is disposed in receiver 405.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

In one example, a delivery device for a collapsible prosthetic heart valve includes a catheter assembly having a compartment for receiving a medical device and an outer shaft having a first end coupled to the catheter assembly. The device further includes an operating handle including a deployment actuator coupled to a second end of the outer shaft, the operating handle having a clip for holding an intermediate portion of the outer shaft in fixed relationship to the operating handle.

The clip may include two parallel ridges defining a receiving space therebetween. The clip may be configured such that, when the outer shaft is held thereby, the catheter assembly and the operating handle are oriented perpendicularly to one another. The operating handle may include a top portion and a bottom portion joined together to form a housing, the clip being formed integrally with the top portion. The outer shaft may extend from a distal end of the operating handle, the clip being disposed adjacent the distal end of the operating handle.

In another example, a loading clip for a delivery device includes a body having a first receiver and a second receiver joined to the first receiver at a neck, the first receiver having a first receiving space configured to accept a first portion of an outer shaft of the delivery device and the second receiver having a second receiving space configured to accept a second portion of the outer shaft of the delivery device.

The first receiving space and the second receiving space may be oriented orthogonally to one another. The first receiving space may be sized to receive multiple portions of the outer shaft. The body may include a flexible metal. The body may include a polymeric material. The body may include acrylonitrile butadiene styrene.

In another example, a loading clip for a delivery device having an operating handle and an outer shaft extending from an end of the operating handle includes a body having a first receiver and a second receiver, the first receiver being coupleable to a portion of the delivery device, and the second receiver being coupleable to a portion of the outer shaft of the delivery device.

The first receiver may be coupleable to the operating handle of the delivery device. The first receiver may be coupleable to the end of the operating handle. The end of the operating may include a boss and the first receiver is coupleable to the boss. The first receiver and the second receiver may be oriented orthogonally to one another.

In another example, a method of loading a collapsible prosthetic heart includes providing a delivery device having a catheter assembly, an operating handle and an outer shaft extending therebetween, the catheter assembly including a compartment adapted to receive the prosthetic heart valve and being spaced from the operating handle by a length of the outer shaft. The outer shaft may be coupled to a clip so that the catheter assembly is at a fixed distance from the operating handle, the fixed distance being less than the length of the outer shaft. The prosthetic heart valve may be loaded into the compartment of the catheter assembly.

The clip may be integrally formed with the operating handle and the coupling step may couple an intermediate section of the outer shaft to the operating handle. The clip may include a first receiver and a second receiver, and the coupling step may include coupling the outer shaft to the second receiver, the method further including coupling the first receiver of the clip to a portion of the operating handle. The clip may include a first receiver and a second receiver, and the coupling step may include coupling a first portion of the outer shaft to the first receiver and a second portion of the outer shaft to the second receiver.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A system for delivery of a collapsible prosthetic heart valve, the system including a delivery device and the collapsible prosthetic heart valve, the delivery device comprising:
a catheter assembly having a compartment in which the collapsible prosthetic heart valve is received;
an outer shaft having a first end coupled to the catheter assembly; and
an operating handle coupled to a second end of the outer shaft, the operating handle defining a longitudinal axis and having an upper housing, a lower housing, a deployment actuator operatively coupled to the outer shaft, and a receiver molded integrally with the upper housing for holding an intermediate portion of the outer shaft in fixed relationship to the operating handle,
wherein the receiver has two parallel ridges defining a receiving space therebetween, the receiving space being located between the deployment actuator and a distal end of the operating handle from which the outer shaft extends, the receiving space extending transverse to the longitudinal axis so that when the intermediate portion of the outer shaft is assembled in the receiving space, the outer shaft does not overlap with the deployment actuator.

2. The system of claim 1, wherein the receiver is configured such that, when the intermediate portion of the outer shaft is held thereby, the intermediate portion of the outer shaft disposed within the receiver, and the operating handle are oriented perpendicularly to one another.

3. The system of claim 1, wherein the two parallel ridges are both perpendicular to the longitudinal axis of the operating handle.

4. The system of claim 1, wherein the receiving space is trough-shaped.

5. The system of claim 1, wherein the receiving space is generally cylindrical.

6. The system of claim 1, wherein the receiving space includes a narrowed opening.

7. The system of claim 1, wherein the receiving space is sized so that the outer shaft is interference fit therein.

8. The system of claim 1, wherein the receiver is configured such that, when the outer shaft is held thereby, the catheter assembly and the operating handle are between 25 and 60 degrees with respect to one another.

9. The system of claim 1, wherein the operating handle has a first width in a lateral direction perpendicular to the longitudinal axis, and the receiver has a second width in the lateral direction, the second width being less than the first width.

* * * * *